US012728121B2

(12) United States Patent
Williams

(10) Patent No.: US 12,728,121 B2
(45) Date of Patent: Sep. 8, 2026

(54) COMPOSITIONS AND METHODS FOR TREATING IDIOPATHIC PULMONARY FIBROSIS

(71) Applicant: Seyltx, Inc., Pittsburgh, PA (US)

(72) Inventor: Mark Williams, Winnipeg, CA (US)

(73) Assignee: Seyltx, Inc., Pittsburgh, PA (US)

( * ) Notice: Subject to any disclaimer, the term of this patent is extended or adjusted under 35 U.S.C. 154(b) by 762 days.

(21) Appl. No.: 17/424,070

(22) PCT Filed: Feb. 14, 2020

(86) PCT No.: PCT/CA2020/050199

§ 371 (c)(1),
(2) Date: Jul. 19, 2021

(87) PCT Pub. No.: WO2020/163966

PCT Pub. Date: Aug. 20, 2020

(65) Prior Publication Data

US 2022/0117951 A1 Apr. 21, 2022

Related U.S. Application Data

(60) Provisional application No. 62/873,723, filed on Jul. 12, 2019, provisional application No. 62/805,755, filed on Feb. 14, 2019.

(51) Int. Cl.
*A61K 31/4453* (2006.01)
*A61P 11/00* (2006.01)

(52) U.S. Cl.
CPC .......... *A61K 31/4453* (2013.01); *A61P 11/00* (2018.01)

(58) Field of Classification Search
CPC .............. A61K 31/136; A61K 31/4184; A61K 31/445; A61K 31/4453; A61K 31/454; A61K 31/4741; A61P 11/00
See application file for complete search history.

(56) References Cited

U.S. PATENT DOCUMENTS

| | | | |
|---|---|---|---|
| 7,547,715 B2 | 6/2009 | Sakai et al. | |
| 7,858,650 B2 | 12/2010 | Yamamoto et al. | |
| 12,472,170 B2 | 11/2025 | Williams | |
| 12,478,618 B1 | 11/2025 | Williams | |
| 2005/0222205 A1 | 10/2005 | Brew et al. | |
| 2008/0268014 A1 | 10/2008 | Garvey et al. | |
| 2015/0272874 A1 | 10/2015 | Sawa et al. | |
| 2018/0215699 A1* | 8/2018 | Humbert | C07C 211/62 |
| 2018/0235931 A1 | 8/2018 | Basta et al. | |

FOREIGN PATENT DOCUMENTS

| | | | | |
|---|---|---|---|---|
| CA | 2938928 A1 | 8/2015 | | |
| CA | 3101853 A1 | 8/2020 | | |
| CA | 3154792 A1 | 8/2020 | | |
| CN | 110251677 A | 9/2019 | | |
| CN | 113438949 A | 9/2021 | | |
| EP | 3923938 A1 | 12/2021 | | |
| GB | 2430434 A | 3/2007 | | |
| JP | 2022520110 A | 3/2022 | | |
| WO | WO-2012020270 A1 * | 2/2012 | | A61K 31/423 |
| WO | 2014/069401 A1 | 5/2014 | | |
| WO | 2015171770 A1 | 11/2015 | | |
| WO | 2018/136554 A1 | 7/2018 | | |

OTHER PUBLICATIONS

Li et al. NMDA Receptor Antagonist Attenuates Bleomycin-Induced Acute Lung Injury. PLoS One. May 5, 2015;10(5):e0125873. (Year: 2015).*
Annual Reports in Medicinal Chemistry (2012) vol. 47: 89-103.
European Search Report, European Application No. 20754897.5, dated Mar. 22, 2022, 7 pages.
Nair and Jacob, "A simple practice guide for dose conversion between animals and human," J Basic Clin Pharm vol. 7 (2):27-31 (2016).
Hashimoto, K. "Activation of sigma-1 receptor chaperone in the treatment of neuropsychiatric diseases and its clinical Implication," J. Pharmacological Sciences, vol. 127:6-9 (2015).
International Preliminary Report on Patentability, PCT/CA2020/050199, dated Aug. 10, 2021, 8 pages.
International Search Report and Written Opinion, PCT/CA2020/050199, dated Apr. 27, 2020, 14 pages.
Mouratis, M. et al., "Modeling pulmonary fibrosis with bleomycin," Current Opinion in Pulmonary Medicine, vol. 17 (5):355-361 (2011).
Abdulqawi, Rayid, et al. An open-label study of the tolerability and potential efficacy of memantine for treating refractory chronic cough. ERJ Open Research 7.3 (2021).
Akwe, J. Pulmonary Effects of Cocaine Use. Journal of Lung, Pulmonary & Respiratory Research. vol. 4, Issue 2, 6 pages (2017).
Anderson, Sandra. et al. Inhaled Medicines: Past, Present, and Future. Pharmacological Reviews 74(1):48-118 (2022).
Avenet, Patrick. et al. Antagonist Properties of the Stereoisomers of Ifenprodil at NR1A/NR2A and NR1A/NR2B Subtypes of the NMDA Receptor Expressed in Xenopus Oocytes. European Journal of Pharmacology 296(2):209-213 (1996).
Belvisi, Maria G. Summary: animal models for cough. Pulm. Pharmacol. Ther. 15: 249-250. (2002).
Brightling, Christopher E. Chronic Cough Due to Nonasthmatic Eosinophilic Bronchitis: ACCP Evidence-based Clinical Practice Guidelines. Chest 129(1):116S-121S (2006).
Bryan, Christopher. Algernon Pharmaceuticals: An update on NP-120 (ifenprodil): A subunit-selective NMDA receptor antagonist for the treatment of cough, American Cough Conference. pp. 1-23. (2023).

(Continued)

*Primary Examiner* — Kara R. Mcmillian
(74) *Attorney, Agent, or Firm* — WILSON SONSINI GOODRICH & ROSATI

(57) ABSTRACT

The use of pharmaceutically active compounds for treating chronic lung diseases including idiopathic pulmonary fibrosis is disclosed. The compounds include NMDA receptor antagonists, glutamate 2b receptor antagonists and sigma receptor agonists. In particular, the use of bromantane, ifenprodil, radiprodil, bemithyl and repirinast are effective in treating idiopathic pulmonary fibrosis. Methods of use thereof are also disclosed.

16 Claims, 3 Drawing Sheets

(56) References Cited

OTHER PUBLICATIONS

Callaway, J. K., et al. Evidence for peripheral mechanisms mediating the antitussive actions of opioids in the guinea pig. General Pharmacology: The Vascular System 22.6: 1103-1108. (1991).
Canning, Brendam J., et al. Encoding of the cough reflex in anesthetized guinea pigs. Am J Physiol Regul Integr Comp Physiol 300: R369-R377. (2011).
Canning, Brendan J. Central Regulation of the Cough Reflex: Therapeutic Implications. Pulmonary Pharmacology & Therapeutics 22(2):75-81 (2009).
Chemical Abstracts Service. CAS Registry No. 808732-98-1. Rislenemdaz. STN Entry Date Oct. 26, 2006.
Chen, Liyan, et al. Detection of mouse cough based on sound monitoring and respiratory airflow waveforms. PloS one 8.3: e59263. (2013).
Chou, Yang-Ling, et al. Central vs. peripheral sites of action of antitussive agents in anesthetized guinea pigs. The FASEB Journal 23: 1011-3. (2009).
Chung, Kian Fan, et al. Cough hypersensitivity and chronic cough. Nature Reviews Disease Primers 8.1: 45. (2022).
Citalopram FDA Label, Reference ID:4933291, 25 pages, Initial U.S. Approval 1998.
Cotton, Imelda. Algernon Pharmaceuticals to present findings of Ifenprodil study for treatment of idiopathic pulmonary fibrosis. Small Caps. Retrieved from: https://smallcaps.ca/agernon-pharmaceuticals-present-findings-ifenprodil-study-treatment-idiopathic-pulmonary-fibrosis/ on Apr. 17, 2024. pp. 1-3. (2022).
Deidda, A. et al. Interstitial lung disease induced by fluoxetine: Systematic review of literature and analysis of Vigiaccess, Eudravigilance and a national pharmacovigilance database, Science Direct Pharmacological Research, vol. 120, 294-301 (2017).
Dere, E. et al. NMDA-Receptor Antagonism Via Dextromethorphan And Ifenprodil Modulates Graded Anxiety Test Performance Of C57BL/6 Mice. Behavioural Pharmacology 14(3):245-249 (2003).
Dicpinigaitis, Peter V., et al. Effect of Memantine on Cough Reflex Sensitivity: Translational Studies in Guinea Pigs and Humans. The Journal of Pharmacology and Experimental Therapeutics, 352: pp. 448-454. (2015).
EP20882816.0 Extended European Search Report dated Jan. 30, 2024.
Escitalopram FDA Label, Reference ID:4036381, 26 pages, Initial U.S. Approval 2002.
Fluvoxamine FDA Label, Reference ID: 3223798, 35 pages, Initial U.S. approval 1994.
Globe Newswire. Algernon Pharmaceuticals to present Phase 2 Ifenprodil Cough Data at the 2023 American Cough Conference. pp. 1-6. (2023).
Grattan, T. J., et al. The effect of inhaled and oral dextromethorphan on citric acid induced cough in man. British journal of clinical pharmacology 39.3: 261-263. (1995).
Inacio, Patricia. NP-120 (ifenprodil) Eases Cough in IPF Patients, Analysis Shows. Pulmonary Fibrosis News. Retrieved from: https://pulmonaryfibrosisnews.com/news/np-120-ifenprodil-eases-cough-ipf-patients-analysis-shows/ on Apr. 17, 2024. pp. 1-8. (2022).
Kocsis, Bernat. Differential role of NR2A and NR2B subunits in NMDA receptor antagonist-induced aberrant cortical gamma oscillations. Biol. Psychiatry, 71(11): pp. 987-995. (2012).
Lamotrigine FDA Label, Reference ID: 4771201, 70 pages, Initial U.S. Approval 1994.
Leonard, B. Sigma receptors and sigma ligands: background to a pharmacological enigma. Pharmacopsychiatry. 37 Suppl 3:S166-70. (2004)—Abstract Only.
Lever, John R. et al. Characterization Of Pulmonary Sigma Receptors By Radioligand Binding. European Journal of Pharmacology 762:118-126 (2015).
Mann, Jennifer. et al. Cough in Idiopathic Pulmonary Fibrosis. Frontiers in Rehabilitation Sciences 2:751798, 1-12 (2021).
Martin Nguyen, Allison, et al. Validation of a visual analog scale for assessing cough severity in patients with chronic cough. Therapeutic advances in respiratory disease 15, 17534666211049743. (2021).
Martinez, Fernando J., et al. Treatment of persistent cough in subjects with idiopathic pulmonary fibrosis (IPF) with gefapixant, a P2X3 antagonist, in a randomized, placebo-controlled clinical trial. Pulmonary therapy 7.2: 471-486. (2021).
Mazzone, Stuart B., et al. Vagal afferent innervation of the airways in health and disease. Physiological reviews 96.3: 975-1024. (2016).
Moe, Aung Aung Kywe, et al. Brainstem processing of cough sensory inputs in chronic cough hypersensitivity. EBioMedicine 100. pp. 1-15. (2024).
Nakanishi, Yuki. et al. 03F-28-4: Modulations Of Cough Reflex Sensitivity Through Airway NMDA Receptor. Journal of Pharmacological Sciences 121:112, p. 1 (2013).
Nguyen, Linda. et al. Dextromethorphan: An Update On Its Utility For Neurological And Neuropsychiatric Disorders. Pharmacology & Therapeutics 159:1-22 (2016).
Oh, S. et al. Dextromethorphan. StatPearls NCBI Bookshelf, pp. 6 (2023).
Ohi, Y. et al. Dextromethorphan Inhibits the Glutamatergic Synaptic Transmission in the Nucleus Tractus Solitarius of Guinea Pigs. J Pharmacol Sci 116, 54-62 (2011).
PCT/CA2020/050306 International Preliminary Report on Patentability dated May 3, 2022.
PCT/CA2020/050306 International Search Report and Written Opinion dated Jun. 23, 2020.
Rashid, Jahidur. et al. Repurposing Rosiglitazone, A PPAR-γ Agonist And Oral Antidiabetic, As An Inhaled Formulation, For The Treatment Of PAH. Journal of Controlled Release 280:113-123 (2018).
Reagan-Shaw, Shannon. et al. Dose Translation From Animal to Human Studies Revisited. The Faseb Journal 22(3):659-661 (2008).
Shapiro, Lindsey. NP-120's Efficacy for IPF Supported by Full Phase 2a Trial Data Analyses. Retrieved from: https://pulmonaryfibrosisnews.com/news/np-120-efficacy-supported-full-phase-2a-trial-data-algernon/ on Apr. 17, 2024. pp. 1-8. (2022).
Smith, Jaclyn A., et al. Antitussive effects of memantine in guinea pigs. Chest 141.4: 996-1002. (2012).
Smith, Jaclyn A. The therapeutic landscape in chronic cough. Lung 202.1: 5-16. (2024).
U.S. Appl. No. 17/771,664 Office Action dated Jan. 21, 2025.
U.S. Appl. No. 17/771,664 Office Action dated Mar. 14, 2025.
U.S. Appl. No. 17/771,664 Office Action dated Sep. 6, 2024.
U.S. Appl. No. 17/771,664 Restriction Requirement dated Jun. 25, 2024.
U.S. Appl. No. 18/811,355 Notice of Allowance dated Sep. 9, 2025.
U.S. Appl. No. 18/811,355 Office Action dated Feb. 7, 2025.
Wang, Jingya, et al. Distinct and common expression of receptors for inflammatory mediators in vagal nodose versus jugular capsaicin-sensitive/TRPV1-positive neurons detected by low input RNA sequencing. PloS one 12.10: e0185985. (2017).
Wei, Yi-Chia, et al. Different FDG-PET metabolic patterns of anti-AMPAR and anti-NMDAR encephalitis: case report and literature review. Brain and behavior 10.3: e01540. (2020).
Zhang, Cheng, et al. Cough and expiration reflexes elicited by inhaled irritant gases are intensified in ovalbumin-sensitized mice. American Journal of Physiology-Regulatory, Integrative and Comparative Physiology 312.5: R718-R726. (2017).

* cited by examiner

Trichrome Score

% Reduction in Fibrosis vs Vehicle

COMPOSITIONS AND METHODS FOR TREATING IDIOPATHIC PULMONARY FIBROSIS

REFERENCE TO RELATED APPLICATIONS

This application is a 35 U.S.C. 371 national stage filing of International Application No. PCT/CA2020/050199, filed on Feb. 14, 2020, which claims priority to U.S. provisional application No. 62/805,755 filed Feb. 14, 2019 and U.S. provisional application No. 62/873,723 filed Jul. 12, 2019, the contents of which are hereby incorporated by reference.

FIELD OF INVENTION

The present invention relates to the use of compounds for treating fibrosis in the lungs, and in particular, the use of Bromantane, Ifenprodil, Radiprodil, Bemithyl, and/or Repirinast for treating chronic lung disease, including idiopathic pulmonary fibrosis.

BACKGROUND

Idiopathic pulmonary fibrosis (IPF) is a form of interstitial lung disease that is characterized by scarring (fibrosis) of the lungs. This results in progressive and irreversible decline in lung operation, including breathing. Symptoms typically include gradual onset of shortness of breath and a dry, chronic cough. Other symptoms include chest pain and fatigue. The causes of IPF is not completely understood. However, factors which increase the risk of IPF include cigarette smoking, acid reflux, and a family history of the condition.

There is currently no cure for IPF and no procedures or medications that can remove the scarring from the lungs. Conventional treatment of IPF tends to focus on slowing the progression of the lung scarring. Such treatment includes pulmonary rehabilitation, supplemental oxygen, and/or use of medications like pirfenidone or nintedanib. Lung transplantation is also an option in severe cases.

The bleomycin (BLM) murine models is probably the most accepted model of pulmonary fibrosis. Intratracheal administration of bleomycin effectively mimics the chronic aspect of pulmonary fibrosis, as well as other characteristics including the presence of hyperplastic alveolar epithelial cells. (Mouratis et al., *Modeling pulmonary fibrosis with bleomycin, Current Opinion in Pulmonary Medicine*: September 2011, Vol 17(5):355-361). In one such model, BLM is initially and directly introduced to the alveolar epithelial cells, to develop neutrophilia and lymphocytes and BLM-induced fibrosis develops after about seven days. In this model, only a single instillation is needed, the disease develops in a short time frame and it has high reproducibility. BLM-induced fibrosis in mice constitutes an animal model of IPF with high degree of similarity to the histopathological characteristics and distribution of lung fibrosis described in human idiopathic pulmonary fibrosis.

The present invention provides a novel use of existing drugs, typically studied and used as potential therapies for other pathologies, for the treatment and/or alleviation of IPF.

SUMMARY OF INVENTION

In one aspect, the present invention provides methods and uses of Bromantane for the treatment or prophylaxis of idiopathic pulmonary fibrosis in a subject.

In another aspect, the present invention provides methods and uses of Ifenoprodil for the treatment or prophylaxis of idiopathic pulmonary fibrosis in a subject.

In another aspect, the present invention provides methods and uses of Radiprodil for the treatment or prophylaxis of idiopathic pulmonary fibrosis in a subject.

In another aspect, the present invention provides methods and uses of Bemithyl for the treatment or prophylaxis of idiopathic pulmonary fibrosis in a subject.

In another aspect, the present invention provides methods and uses of Repirinast for the treatment or prophylaxis of idiopathic pulmonary fibrosis in a subject.

In an embodiment of the invention, a glutamate 2b receptor (Glut2B or GluN2B) antagonist for the treatment or prophylaxis of idiopathic pulmonary fibrosis in a subject. The Glut2B antagonist may be one or more of Ifenprodil, Radiprodil, Traxoprodil, Rislenmdaz, Eliprodil, Ro-25-6981, and BMT-108908, EVT-101, CP101-606, MK-0657, EVT-103, and AZD 6765 (Annual Reports in Medicinal Chemistry (2012) Volume 47: 94-103).

BRIEF DESCRIPTION OF THE FIGURES

Exemplary embodiments are illustrated in referenced figures of the drawings. It is intended that the embodiments and figures disclosed herein are to be considered illustrative rather than restrictive.

DETAILED DESCRIPTION

Figure 1:
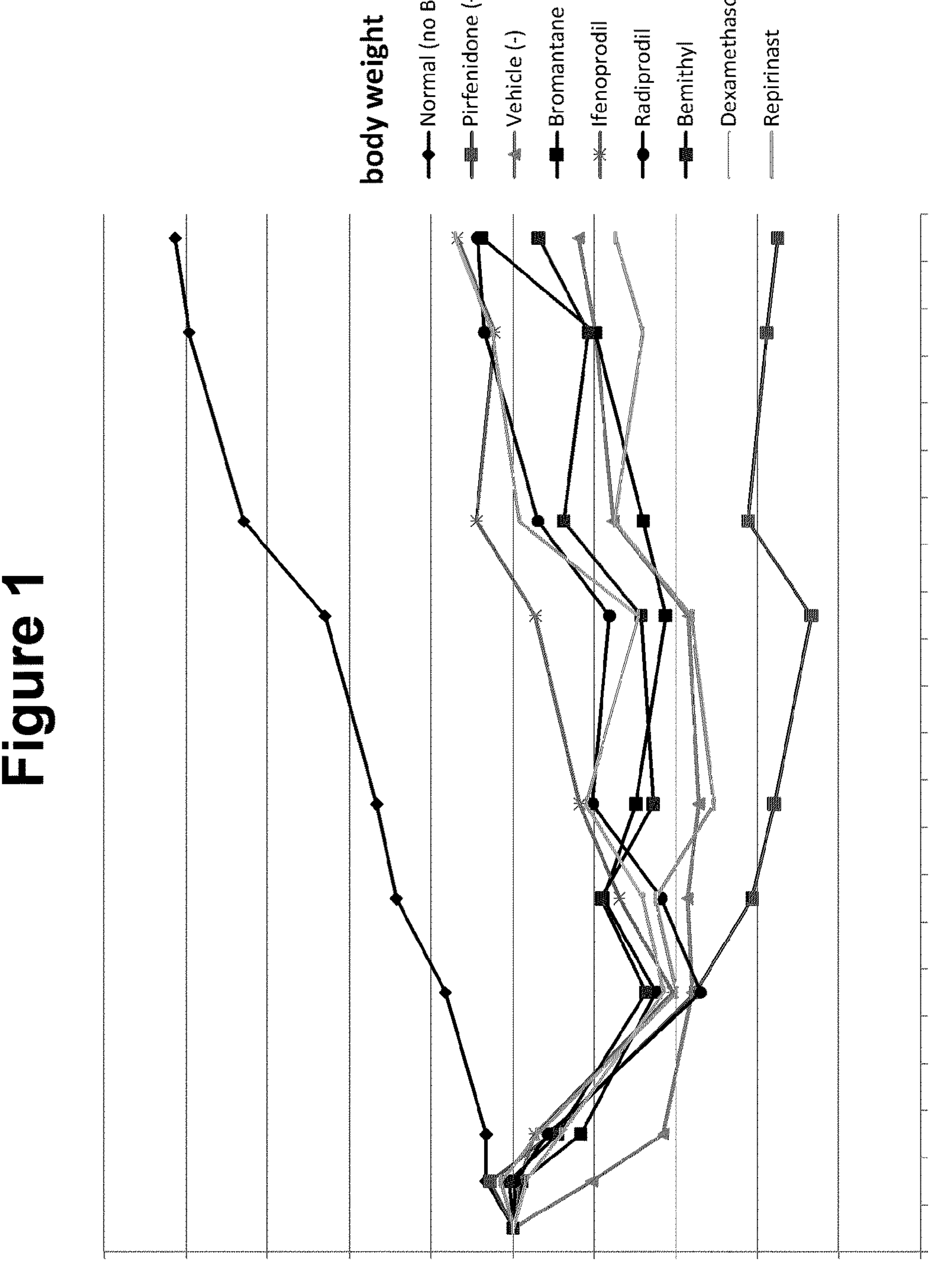
FIG. 1 is a line graph comparing the mean percentage change in body weights in grams for the experimental treatment groups of mice, using test compounds Bromantane, Ifenoprodil, Radiprodil, Bemithyl, Dexamethasone, and Repirinast, compared to the Normal (no BLM) control group, the BLM-Vehicle control group, and the Pirfenidone positive control group.

The inventor has found certain pharmacologic compounds approved for use in other pathologies are useful in inhibiting or alleviating fibrosis in the lungs and appear useful in the prophylaxis and/or treatment of interstitial lung disease.

It was found that in BLM-induced fibrosis, the level of pulmonary inflammation is inhibited or alleviated. Based on the experimental results described herein, it is shown that the compounds described are useful in the prophylaxis and/or treatment of interstitial lung disease or idiopathic pulmonary fibrosis.

The currently used therapy for lung fibrosis and idiopathic pulmonary fibrosis is administering the pharmacologic compound Pirfenidone, which was used as a positive control in the experimental examples described herein.

Pirfenidone, 5-methyl-1-phenylpyridin-2(1H)-one, is an orally active synthetic antifibrotic agent known in the art for inhibiting collagen formation used to treat idiopathic pulmonary fibrosis. The chemical structure of Pirfenidone is:

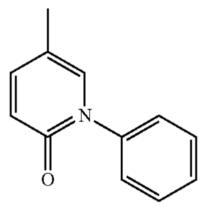

Dexamethasone, $NaN_3$ or $C_{22}H_{29}FO_5$, is an orally active synthetic anti-inflammatory agent known in the art for inhibiting inflammation and used as a positive control in idiopathic pulmonary fibrosis models. The chemical structure of Dexamethasone is:

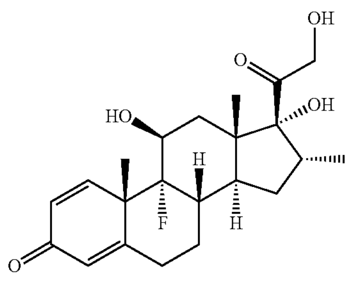

The examples and data below show the effects of inhibiting or alleviating lung fibrosis by administering a therapeutically effective amount of Bromantane, Ifenoprodil, Radiprodil, Bemithyl, and Repirinast. These compounds described herein are existing drugs, typically known for treatment of non-pulmonary related conditions.

Use of Bromantane

Bromantane, N-(4-bromophenyl)adamantan-2-amine, is known in the art as a psychostimulant and anxiolytic drug of the adamantane family. The chemical structure of Bromantane is:

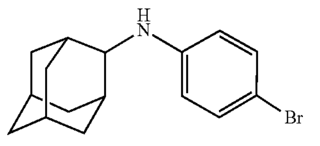 [SMILES: Brc1ccc(NC2C3CC4CC(C3)CC2C4)cc1]

In one aspect, the present invention provides a use and method of treatment or prophylaxis of idiopathic pulmonary fibrosis in a subject with Bromantane or a pharmaceutically acceptable variation thereof. The interstitial lung disease may be idiopathic pulmonary fibrosis (IPF), among others.

In an embodiment, the amount of Bromantane used is between 0.8 and 5 mg per kg of the subject per day. In a preferred embodiment, the amount of Bromantane used is between 1.7 to 3.3 mg per kg of the subject per day. In a further preferred embodiment, the amount of Bromantane used is about 1.7 mg per kg of the subject per day.

The Bromantane, or pharmaceutically acceptable variation thereof, may be administered to the subject orally, intravenously or in a manner known in the art. The Bromantane, or pharmaceutically acceptable variation thereof, may also be administered with one or more pharmaceutically acceptable excipients.

Use of Ifenoprodil

Ifenprodil, 4-[2-(4-benzylpiperidin-1-ium-1-yl)-1-hydroxypropyl] phenol; 2,3,4-trihydroxy-4-oxobutanoate, is known in the art as a selective NMDA receptor (glutamate) antagonist. Ifenprodil was originally (in the early 1970's) developed as a vasodilator. Ifenprodil is currently being studied for treatment of adolescent PTSD. The chemical structure is:

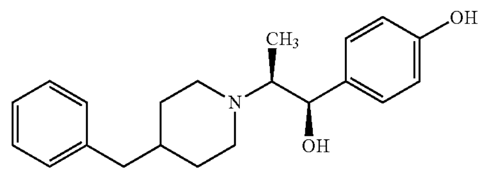 [SMILES: C[C@@H]([C@H](O)c1ccc(O)cc1)N1CCC(Cc2ccccc2)CC1]

In some embodiments tested in the examples herein, Ifenprodil hemitartrate having the following structure was used:

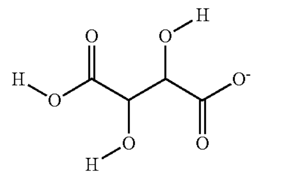

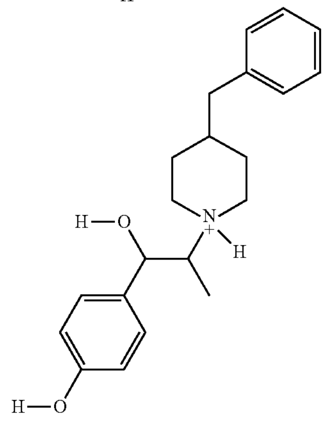

In one aspect, the present invention provides a use and method of treatment or prophylaxis of idiopathic pulmonary fibrosis in a subject with Ifenoprodil or a pharmaceutically acceptable variation thereof. The interstitial lung disease may be idiopathic pulmonary fibrosis (IPF), among others.

In an embodiment, the amount of Ifenoprodil used is between 0.6 and 5 mg per kg of the subject per day. In a preferred embodiment, the amount of Ifenoprodil used is between 0.8 to 3 mg per kg of the subject per day. In a further preferred embodiment, the amount of Ifenoprodil used is about 1 mg per kg of the subject per day.

The Ifenoprodil, or pharmaceutically acceptable variation thereof, may be administered to the subject orally, intravenously or in a manner known in the art. The Ifenoprodil, or pharmaceutically acceptable variation thereof, may also be administered with one or more pharmaceutically acceptable excipients.

Use of Radiprodil

Radiprodil, 2-[4-[(4-fluorophenyl)methyl]piperidin-1-yl]-2-oxo-N-(2-oxo-3H-1,3-benzoxazol-6-yl)acetamide, is known in the art as an NMDA receptor antagonist. It has been used in trials studying the treatment of Infantile Spasms (IS) and Diabetic Peripheral Neuropathic Pain. The chemical structure of Radiprodil is:

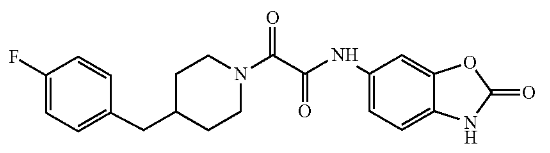 [SMILES: O=C(Nc1ccc2[nH]c(=O)oc2c1)C(=O)N1CCC(Cc2ccc(F)cc2)CC1]

In one aspect, the present invention provides a use and method of treatment or prophylaxis of idiopathic pulmonary fibrosis in a subject with Radiprodil or a pharmaceutically acceptable variation thereof. The interstitial lung disease may be idiopathic pulmonary fibrosis (IPF), among others.

In an embodiment, the amount of Radiprodil used is between 1.6 and 3.3 mg per kg of the subject per day. In a preferred embodiment, the amount of Radiprodil used is about 2.5 mg per kg of the subject per day. In a further preferred embodiment, the amount of Radiprodil used is about 2.25 mg per kg of the subject par day.

The Radiprodil, or pharmaceutically acceptable variation thereof, may be administered to the subject orally, intravenously or in a manner known in the art. The Radiprodil, or pharmaceutically acceptable variation thereof, may also be administered with one or more pharmaceutically acceptable excipients.

Use of Bemithyl

Bemithyl, 2-Ethylsulfanyl-1H-benzoimidazole, is known in the art as a synthetic actoprotector, antioxidant, and antimutagenic, and is often used to increase physical performance. The chemical structure of Bemithyl is:

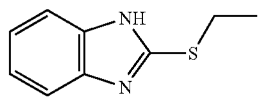

In one aspect, the present invention provides a use and method of treatment or prophylaxis of idiopathic pulmonary fibrosis in a subject with Bemithyl or a pharmaceutically acceptable variation thereof. The interstitial lung disease may be idiopathic pulmonary fibrosis (IPF), among others.

In an embodiment, the amount of Bemithyl used is between 0.5 to 50 mg per kg of the subject per day. In a preferred embodiment, the amount of Bemithyl used is between 1 to 30 mg per kg of the subject per day. In a further preferred embodiment, the amount of Bemithyl used is between 4 to 25 mg per kg of the subject per day. In a yet further preferred embodiment, the amount of Bemithyl used is between 8 to 17 mg per kg of the subject per day. In a still further preferred embodiment, the amount of Bemithyl used is about 17 mg per kg of the subject per day.

The Bemithyl, or pharmaceutically acceptable variation thereof, may be administered to the subject orally, intravenously or in a manner known in the art. The Bemithyl, or pharmaceutically acceptable variation thereof, may also be administered with one or more pharmaceutically acceptable excipients.

Use of Repirinast

Repirinast, Isopentyl 7,8-dimethyl-4,5-dioxo-5,6-dihydro-4H-pyrano[3,2-c]quinoline-2-carboxylate, is known in the art as an is an antihistamine. The chemical structure of Repirinast is:

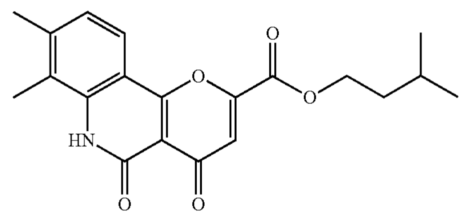 [SMILES: Cc1ccc2c([nH]c(=O)c3c(=O)cc(C(=O)OCCC(C)C)oc32)c1C]

In one aspect, the present invention provides a use and method of treatment or prophylaxis of idiopathic pulmonary fibrosis in a subject with Repirinast or a pharmaceutically acceptable variation thereof. The interstitial lung disease may be idiopathic pulmonary fibrosis (IPF), among others.

In an embodiment, the amount of Repirinast used is between 1 to 50 mg per kg of the subject per day. In a preferred embodiment, the amount of Repirinast used is between 2.5 to 10 mg per kg of the subject per day. In a further preferred embodiment, the amount of Repirinast used is about 7.5 mg per kg of the subject per day.

The Repirinast, or pharmaceutically acceptable variation thereof, may be administered to the subject orally, intravenously or in a manner known in the art. The Repirinast, or pharmaceutically acceptable variation thereof, may also be administered with one or more pharmaceutically acceptable excipients.

In an embodiment of the invention, a glutamate 2b receptor (Glut2B or GluN2B) antagonist for the treatment or prophylaxis of idiopathic pulmonary fibrosis in a subject. The Glut2B antagonist may be one or more of Ifenprodil, Radiprodil, Traxoprodil, Rislenmdaz, Eliprodil, Ro-25-6981, and BMT-108908, EVT-101, CP101-606, MK-0657, EVT-103, and AZD 6765 (Annual Reports in Medicinal Chemistry (2012) Volume 47: 94-103).

In another aspect of the invention, ifenprodil is a known to exhibit NDMA receptor antagonism (GluN1 and more specifically GlunN2B subunits) and sigma receptor agonist (more specifically subtype 1) activity. Sigma receptors are intracellular chaperones that reside in the endoplasmic reticulum of a cell. Thus molecules with similar activity have anti-fibrotic effects and treat IPF. Representative sigma receptor agonists include selective serotonin reuptake inhibitors (SSRI) such as fluvoxamine, fluoxetine, excitalpram and donepezil (J. Pharmacological Sciences (2015) 127:6-9).

Use in Combination

In another aspect, the present invention provides a use and method of treatment or prophylaxis of idiopathic pulmonary fibrosis in a subject with one or more of Bromantane, Ifenoprodil, Radiprodil, Bemithyl, Traxoprodil, Rislenmdaz, Eliprodil, Ro-25-6981, and BMT-108908, EVT-101, CP101-606, MK-0657, EVT-103, and AZD 6765, in combination. In another aspect, the present invention provides a use and method of treatment or prophylaxis of idiopathic pulmonary fibrosis in a subject with one or more of Bromantane, Ifenoprodil, Radiprodil, Bemithyl, and Dexamethasone in combination with one or more of Dexamethasone, pirfenidone and nintedanib.

Repirinast in combination with one or more of: anti-inflammatory drugs, immune system suppressors, antibiotics, anti-diarrheals, pain relievers, iron supplements, vitamin B-12 shots, and calcium and vitamin D supplements.

The term "therapeutically effective amount" used herein refers to the amount of an active ingredient sufficient to confer a desired prophylactic or therapeutic effect in a treated subject. In some embodiments, the effective amount is determined, for example, based on the administration route and frequency, body weight and species of the subject receiving the pharmacologic compound.

In some embodiments, an effective amount of the pharmacologic compound is formulated with a pharmaceutically acceptable vehicle and administered to the subject. The term "pharmaceutically acceptable" used herein means that the vehicle is known in the art as compatible with the pharmacologic compound while also being safe to the subject receiving the treatment. In some embodiments, the pharmaceutically acceptable vehicle is determined by persons skilled in the art evaluating, for example, the solubility of the pharmacologic compound in said vehicle.

Embodiments of the present invention are further described with reference to the following examples, which are intended to be illustrative and not limiting in nature.

Example—Materials and Methods

The mouse species or strain was Mouse/C57BL/6, the mice being 8-10 week old males. Nine groups of 10 mice each were obtained from Charles River Laboratories. Each group was randomized based on body weight. Bleomycin (BLM) was obtained from Euroasias.

The mice were maintained in a controlled environment with a temperature of 70-72° F., humidity 30-70%, with a photocycle of 12 hours of light and 12 hours of dark. They were provided with TEKLAD 2018-Global 18% diet and Arrowhead drinking water ad libitium.

The mice were anesthetized with isoflurane/O2 mixture. Bleomycin (BLM) was then administered to the mice intratracheally (PennCentury)—single bolus, at 2.5 U/kg body weight in 50 μl sterile saline.

Seven days after the bleomycin is administered, and fibroblasts have generally proliferated, six of the nine groups of IT bleomycin challenged mice were be dosed orally (p.o.) once a day with Bromantane, Ifenoprodil, Radiprodil, Bemithyl, Dexamethasone, or Repirinast at specified amounts per kg of body weight (mg/kg) daily for 14 consecutive days. The amounts are set out in Table 1 below. The vehicle used was 0.5% carboxymethyl cellulose (CMC). Prifenidone was also prepared in 0.5% CMC and administrated orally once a day to one of the nine IT bleomycin challenged mice groups beginning for 14 consecutive days. Vehicle and no-BLM control groups received 0.5% CMC orally for 14 consecutive days.

TABLE 1

| | Groups | Once daily oral dosing mg/kg |
|---|---|---|
| 1 | Normal (no BLM) | N/A |
| 2 | Prifenidone (+) | 300 (as per BMC Pulm Med. 2017 Apr. 18; 17(1): 63) |
| 3 | Vehicle (−) | N/A |
| 4 | Bromantane | 20 |
| 5 | Ifenoprodil | 30 |
| 6 | Radiprodil | 30 |
| 7 | Bemithyl | 200 |
| 8 | Dexamethasone | 0.25 |
| 9 | Repirinast | 90 |

On day 21 of the study, 4 hours after the last dose, the mice were sacrificed and plasma was collected and frozen for cytokine analysis (testing for IL-6, IL-12, TGFβ, IL-13 proteins, or fibrosis markers). Bronchoalveolar lavage fluid (BALF) was collected and frozen for optional cytokine analyses and cell counts pending the initial data. The lungs were then excised, weighed and fixed in formalin. Gomori's Trichrome stain, a histological stain, was used to determine collagen content.

The dose selected for the animal studies was determined by taking the maximum known human daily dose, dividing by the average weight of an adult (~60 kg) to get a human mg/kg dose. Then that number was multiplied by 12 to convert to a mouse dose based on conventional dosing tables. See Nair and Jacob, *J Basic Clin Pharm* March 2016-May 2016, 7(2):27-31.

For example:

Daily dose of Radiprol=45 mg three times a day (TID) for diabetic neuropathy=135 mg/day Max daily human dose=135/60=2.25 mg/kg Mouse dose=2.25×12=27 mg/kg/day (increased to 30 to match Ifenprodil)

The following measurements and assessments were taken for each mouse.

Body Weight: The body weights were measured over 21 days using a laboratory balance.

Trichrome Score: A trichrome score measures the level of scarring to the lungs caused by the disease. The greater the trichrome score, the greater the scarring.

Formalin fixed lung samples were submitted to affiliated histopathology laboratory for histopathological analysis subjected Gomori's Trichrome stain, a histological stain, which was used to determine collagen content.

Each lung was divided into ten sections. All ten sections were stained and evaluated. A board certified veterinarian pathologist assessed the presence of lung fibrosis and severity score—The expression of collagen (associated with fibrosis) is determined from the ratio of the stained area versus the total area of the lung section.

Mortality Rate: the mortality rate in each group was also observed over 21 days.

Results

Body Weight

The changes in body weights are presented in FIG. 1, Tables 3 and 4 and Appendix A. The decrease in body weight were observed from day 1 till day 5 and then started recovering. Differences were observed with the groups treated with Ifenprodil (30 mg/kg)] Radiprodil (30 mg/kg), Bemithyl (200 mg/kg), and Dexamethasone (0.25 mg/kg). They showed improvement beginning on Day 5 as compared to the BLM-vehicle group. Bromantane (20 mg/kg) also showed improvement beginning Day 5, with the exception of Day 15 as compared to the BLM-vehicle group. No significant differences were observed between treatment group Repirinast and BLM-vehicle group. Unexpectedly, the Pirfenidone group (300 mg/kg) showed significant deterioration in body weight throughout the trial.

Trichrome Score

Figure 2:
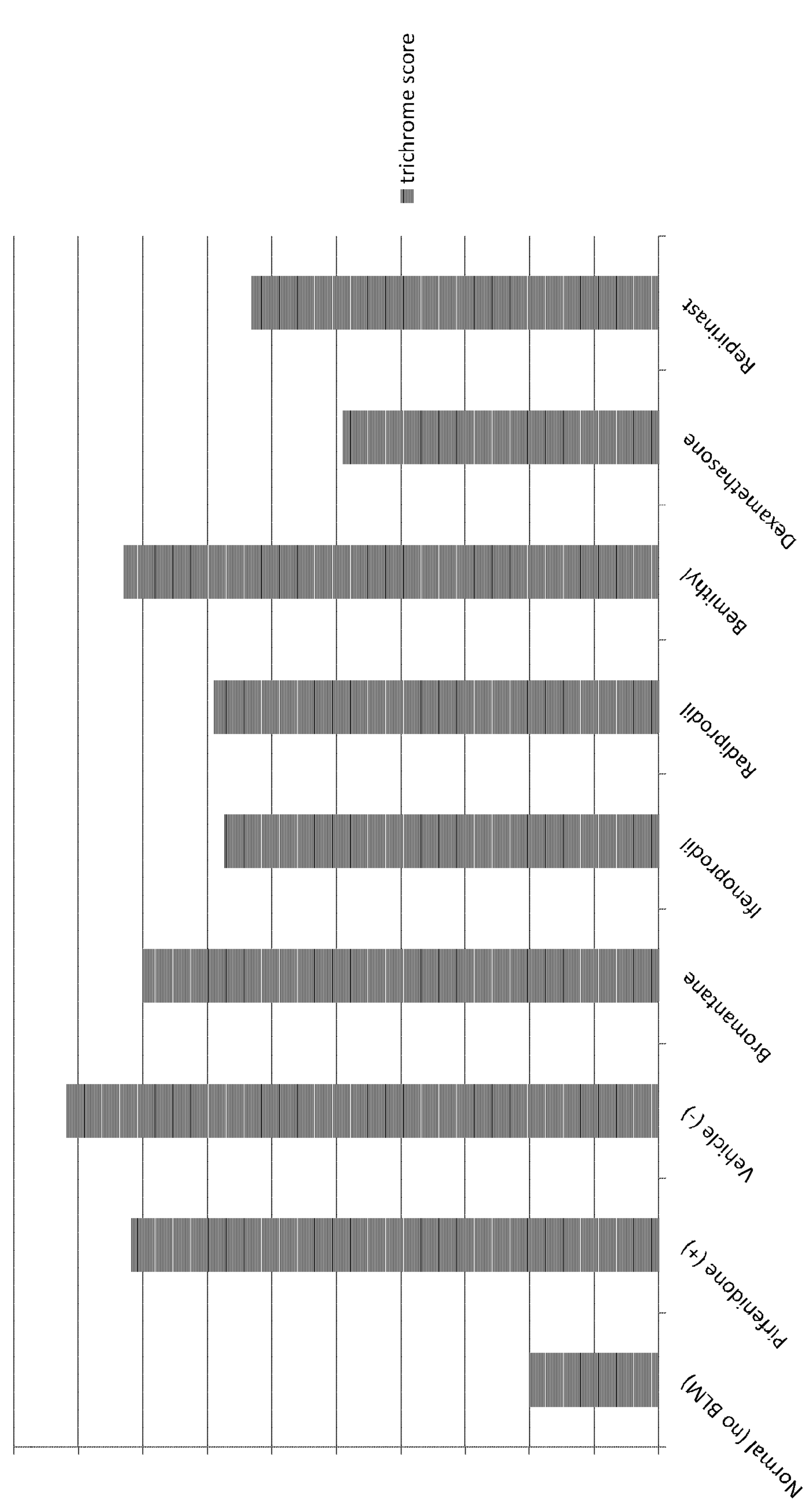
FIG. 2 is a column graph comparing the mean Trichrome Score data, for the experimental treatment groups of mice, using test compounds Bromantane, Ifenoprodil, Radiprodil, Bemithyl, Dexamethasone, and Repirinast, compared to the Normal (no BLM) control group, the BLM-Vehicle control group, and the Pirfenidone positive control group.

The Trichrome score data are presented in FIG. 2, Table 5 and Appendix B. The Trichrome score measured . . . . No significant differences were observed between treatment groups and BLM-vehicle group though the response was better with Dexamethasone (0.25 mg/kg) and Repirinast (90 mg/kg), followed by Ifenprodil (30 mg/kg), and Radiprodil (30 mg/kg) treated groups.

TABLE 5

| Trichrome Score Average | | |
|---|---|---|
| | Trichrome score | % reduction in fibrosis |
| Normal (no BLM) | 1.00 | N/A |
| Pirfenidone (+) | 4.09 | 13.9 |
| Vehicle (−) | 4.59 | 0 |
| Bromantane | 4.00 | 16.4 |
| Ifenoprodil | 3.37 | 34.0 |
| Radiprodil | 3.45 | 31.8 |
| Bemithyl | 4.14 | 12.5 |
| Dexamethasone | 2.45 | 59.6 |
| Repirinast | 3.16 | 39.8 |

An example of how reduction in fibrosis for Pirfenidone was calculated is as follows:

% reduction=100−(trichrome score Pirfenidone−trichrome score normal) divided by (trichrome score vehicle−trichrome score normal)

Percent Survival

Mortality is an important endpoint for IPF patients. The percent survival data is presented in FIG. 6 and Table ##. The percent survival was higher with the treatment group treated with Dexamethasone (0.25 mg/kg) and Repirinast (90 mg/kg), followed by Ifenprodil (30 mg/kg), and Radiprodil (30 mg/kg).

TABLE 6

| Survival Data | | |
|---|---|---|
| | Fatality Number | Percent Fatality |
| Normal (no BLM) | 0/10 | 0 |
| Pirfenidone (+) | 2/10 | 20% |
| Vehicle (−) | 2/10 | 20% |
| Bromantane | 3/10 | 30% |
| Ifenoprodil | 0/10 | 0 |
| Radiprodil | 2/10 | 20% |
| Bemithyl | 1/10 | 10% |
| Dexamethasone | 2/10 | 20% |
| Repirinast | 1/10 | 10% |

Overall

Figure 3:
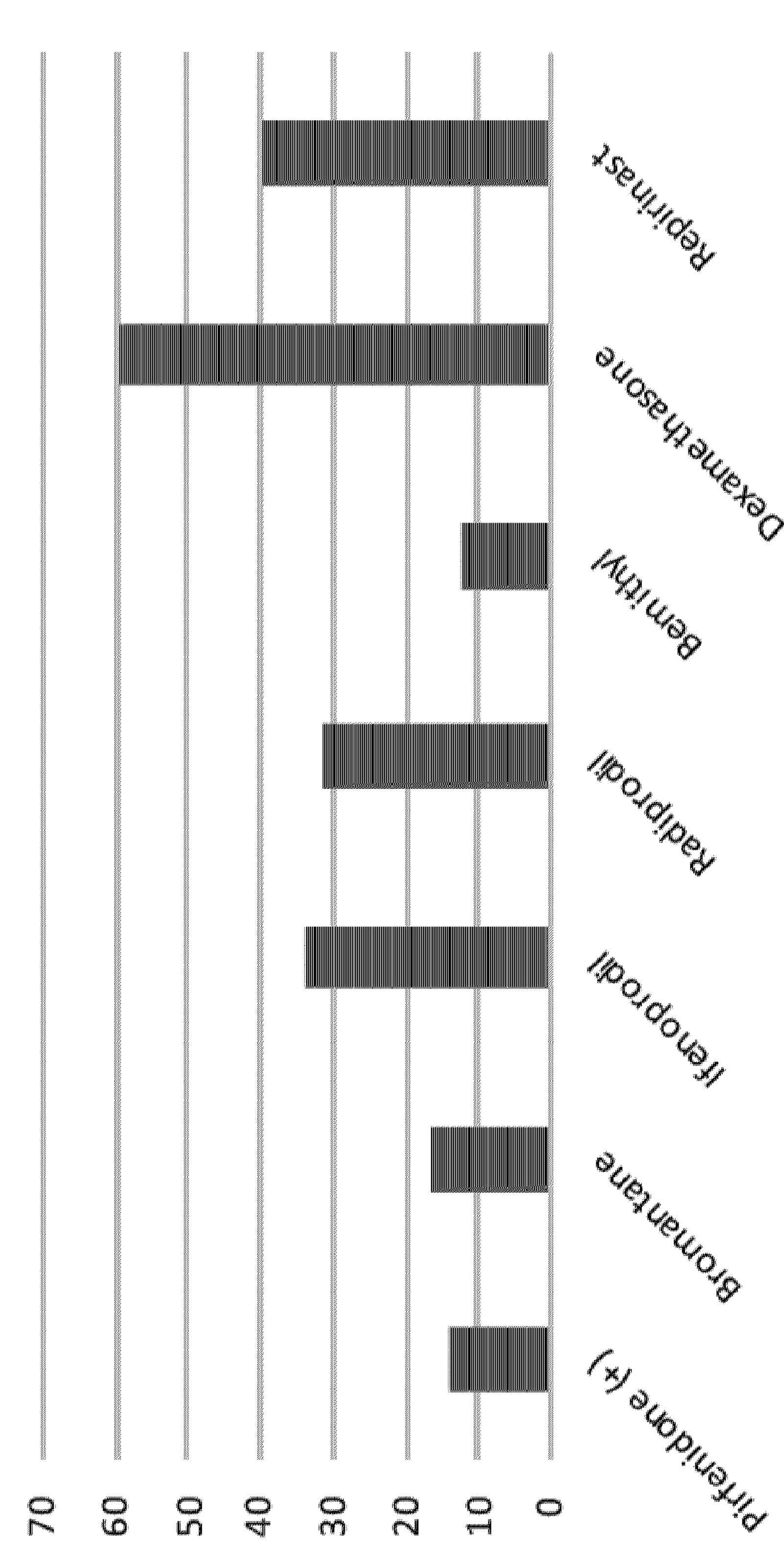
FIG. 3 is a column graph comparing the percent reduction in fibrosis for the experimental treatment groups of mice, using test compounds Bromantane, Ifenoprodil, Radiprodil, Bemithyl, Dexamethasone, and Repirinast, compared to the BLM-Vehicle control group and the Pirfenidone positive control group.

The fibrosis percent reduction analysis is presented in FIG. 3 and Appendix C. The percent reduction in lung fibrosis in comparison to the BLM-vehicle group was higher with the treatment group treated with Dexamethasone (0.25 mg/kg) and Repirinast (90 mg/kg), followed by Ifenprodil (30 mg/kg), and Radiprodil (30 mg/kg).

CONCLUSIONS

In conclusion, oral administration of Dexamethasone at 0.25 mg/kg, Repirinast at 90 mg/kg, Ifenproodil at 30 mg/kg and Rediprodil at 30 mg/kg showed improvement in lung fibrosis as well as in the loss of body weight, Trichrome score and mortality as compared to BLM-vehicle. The improvement was generally most pronounced with the groups treated with Dexamethasone and Repirinast.

Oral administration of Pirfenidone at 300 mg/kg showed minimal improvement in the loss of body weight and trichrome index as compared to BLM-vehicle.

Throughout the following description, specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are consistent with the broadest interpretation of the specification as a whole.

TABLE 3

| Body Weight (g) | | | | | | | | | | |
|---|---|---|---|---|---|---|---|---|---|---|
| | 7-Nov | 8-Nov | 9-Nov | 12-Nov | 14-Nov | 16-Nov | 20-Nov | 22-Nov | 26-Nov | 28-Nov |
| Normal (no BLM) | 23.6 | 24.0 | 24.0 | 24.5 | 25.1 | 25.3 | 25.9 | 26.9 | 27.6 | 27.8 |
| Pirfenidone (+) | 24.0 | 24.2 | 23.5 | 21.7 | 21.0 | 20.8 | 20.3 | 21.1 | 20.9 | 20.7 |
| Vehicle (−) | 25.1 | 24.2 | 23.3 | 22.9 | 23.0 | 22.8 | 23.0 | 23.9 | 24.1 | 24.3 |
| Bromantane | 24.8 | 24.7 | 24.0 | 23.1 | 23.7 | 23.3 | 22.9 | 23.2 | 23.8 | 25.2 |
| Ifenoprodil | 24.4 | 24.3 | 24.1 | 22.4 | 23.1 | 23.6 | 24.1 | 24.9 | 24.6 | 25.1 |
| Radiprodil | 23.6 | 23.6 | 23.2 | 21.3 | 21.8 | 22.6 | 22.4 | 23.3 | 24.0 | 24.0 |
| Bemithyl | 24.6 | 24.7 | 24.1 | 23.0 | 23.5 | 22.9 | 23.1 | 24.0 | 23.7 | 24.3 |
| Dexamethasone | 24.3 | 24.1 | 23.7 | 22.4 | 22.7 | 23.4 | 22.7 | 24.2 | 24.5 | 25.0 |
| Repirinast | 23.5 | 23.7 | 23.2 | 21.5 | 21.8 | 21.1 | 21.4 | 22.3 | 21.9 | 22.3 |

TABLE 4

| Percent Change in Body Weight | | | | | | | | | | |
|---|---|---|---|---|---|---|---|---|---|---|
| | 7-Nov | 8-Nov | 9-Nov | 12-Nov | 14-Nov | 16-Nov | 20-Nov | 22-Nov | 26-Nov | 28-Nov |
| Normal (no BLM) | 0.0 | 0.3 | 0.3 | 0.8 | 1.4 | 1.7 | 2.3 | 3.3 | 4.0 | 4.1 |
| Pirfenidone (+) | 0.0 | 0.3 | −0.5 | −2.2 | −2.9 | −3.2 | −3.7 | −2.9 | −3.1 | −3.2 |
| Vehicle (−) | 0.0 | −1.0 | −1.8 | −2.2 | −2.1 | −2.3 | −2.2 | −1.2 | −1.0 | −0.8 |

TABLE 4-continued

| | Percent Change in Body Weight | | | | | | | | | |
|---|---|---|---|---|---|---|---|---|---|---|
| | 7-Nov | 8-Nov | 9-Nov | 12-Nov | 14-Nov | 16-Nov | 20-Nov | 22-Nov | 26-Nov | 28-Nov |
| Bromantane | 0.0 | −0.1 | −0.8 | −1.8 | −1.1 | −1.5 | −1.9 | −1.6 | −1.0 | 0.4 |
| Ifenoprodil | 0.0 | −0.1 | −0.3 | −2.0 | −1.3 | −0.8 | −0.3 | 0.5 | 0.2 | 0.7 |
| Radiprodil | 0.0 | 0.0 | −0.4 | −2.3 | −1.8 | −1.0 | −1.2 | −0.3 | 0.3 | 0.4 |
| Bemithyl | 0.0 | 0.0 | −0.6 | −1.6 | −1.1 | −1.7 | −1.6 | −0.6 | −0.9 | −0.3 |
| Dexamethasone | 0.0 | −0.2 | −0.6 | −1.9 | −1.6 | −0.9 | −1.5 | −0.1 | 0.3 | 0.7 |
| Repirinast | 0.0 | 0.2 | −0.3 | −2.0 | −1.8 | −2.5 | −2.2 | −1.3 | −1.6 | −1.3 |

What is claimed is:

1. A method for the treatment or prophylaxis of interstitial lung disease in a subject comprising administering an effective amount of ifenprodil to the subject, wherein the method does not comprise administration of an NMDA receptor antagonist other than ifenprodil.

2. The method of claim 1, wherein the amount of ifenprodil is from 0.1 mg per kg of the subject to 5 mg per kg of the subject.

3. The method of claim 2, wherein the amount of ifenprodil is from 0.5 mg per kg of the subject to 3 mg per kg of the subject.

4. The method of claim 3, wherein the amount of ifenprodil is about 1 mg per kg of the subject.

5. The method of claim 3, wherein the amount of ifenprodil is about 2 mg per kg of the subject.

6. The method of claim 3, wherein the amount of ifenprodil is about 3 mg per kg of the subject.

7. The method of claim 1, wherein the interstitial lung disease is idiopathic pulmonary fibrosis.

8. The method of claim 1, wherein the amount of the ifenprodil is from 0.6 mg per kg of the subject to 5 mg per kg of the subject.

9. The method of claim 1, wherein the amount of the ifenprodil is from 0.8 mg per kg of the subject to 3 mg per kg of the subject.

10. The method of claim 1, wherein the method comprises administering from 0.6 mg of the ifenprodil per kg of the subject per day to 5 mg of the ifenprodil per kg of the subject per day.

11. The method of claim 10, wherein the method comprises administering from 0.8 mg of the ifenprodil per kg of the subject per day to 3 mg of the ifenprodil per kg of the subject per day.

12. The method of claim 10, wherein the method comprises administering about 1 mg of the ifenprodil per kg of the subject per day.

13. The method of claim 1, wherein the ifenprodil has the following chemical structure:

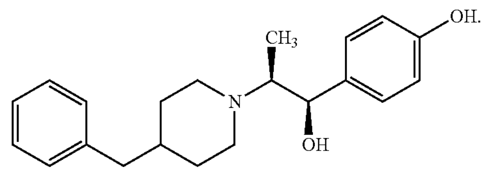 [SMILES: C[C@@H]([C@H](O)c1ccc(O)cc1)N1CCC(Cc2ccccc2)CC1]

14. The method of claim 1, wherein the method comprises administering the ifenprodil orally.

15. The method of claim 1, wherein the method comprises administering the ifenprodil intravenously.

16. A method for the treatment or prophylaxis of interstitial lung disease in a subject comprising administering an effective amount of ifenprodil or a pharmaceutically acceptable variation thereof to the subject, wherein the ifenprodil or the pharmaceutically acceptable variation thereof is ifenprodil hemitartrate, wherein the method does not comprise administration of an NMDA receptor antagonist other than ifenprodil or the pharmaceutically acceptable variation thereof.

* * * * *